United States Patent
Li (10) Patent No.: US 12,042,265 B2
(45) Date of Patent: Jul. 23, 2024

(54) OPTICAL RESPIRATION RATE DETECTION DEVICE CAPABLE OF DETERMINING DENOISING RANGE

(71) Applicant: PixArt Imaging Inc., Hsin-Chu County (TW)

(72) Inventor: Ming-Chang Li, Hsin-Chu County (TW)

( * ) Notice: Subject to any disclaimer, the term of this patent is extended or adjusted under 35 U.S.C. 154(b) by 0 days.

(21) Appl. No.: 18/202,965

(22) Filed: May 29, 2023

(65) Prior Publication Data
US 2023/0293041 A1 Sep. 21, 2023

Related U.S. Application Data

(60) Division of application No. 16/412,500, filed on May 15, 2019, now Pat. No. 11,701,027, which is a continuation-in-part of application No. 15/132,389, filed on Apr. 19, 2016, now abandoned.

(30) Foreign Application Priority Data

Jun. 1, 2015 (TW) .................................. 104117736

(51) Int. Cl.
*A61B 5/08* (2006.01)
*A61B 5/00* (2006.01)

(52) U.S. Cl.
CPC .......... *A61B 5/0816* (2013.01); *A61B 5/0077* (2013.01); *A61B 5/721* (2013.01); *A61B 2562/0219* (2013.01)

(58) Field of Classification Search
CPC .......... A61B 5/0816; A61B 2562/0219; A61B 5/721; A61B 5/0077
See application file for complete search history.

(56) References Cited

U.S. PATENT DOCUMENTS

| | | | |
|---|---|---|---|
| 10,004,427 B1* | 6/2018 | Shoeb .................. | A61B 5/0816 |
| 2003/0163054 A1* | 8/2003 | Dekker ................ | A61B 5/0816 |
| | | | 600/502 |
| 2011/0066037 A1* | 3/2011 | Banet .................... | A61B 5/1116 |
| | | | 600/484 |
| 2011/0071406 A1* | 3/2011 | Addison .............. | A61B 5/0205 |
| | | | 600/529 |

OTHER PUBLICATIONS

Hung et al.; Estimation of respiratory waveform using an accelerometer; date of conference May 14-17, 2008; 2008 5th IEEE International Symposium on Biomedical Imaging: From Nano to Macro; p. 1493-1496 (Year: 2008).*

* cited by examiner

*Primary Examiner* — Chao Sheng
(74) *Attorney, Agent, or Firm* — Bruce Stone LLP; Joseph A. Bruce (57) ABSTRACT

A respiration rate detection device including a photoplethysmography (PPG) detector, an acceleration detector and a processing unit is provided. The processing unit calculates an acceleration peak frequency in an acceleration frequency spectrum, and takes a PPG acceleration peak frequency in a PPG frequency spectrum corresponding to the acceleration peak frequency as a respiration rate.

7 Claims, 6 Drawing Sheets

| SNR₁ | W₁~Wₙ 1st combination |
| SNR₂ | W₁~Wₙ 2nd combination |
| ⋮ | ⋮ |
| SNRₙ | W₁~Wₙ Nth combination |

$$Nb_2 = R_1 \times W_1 + R_2 \times W_2 + \cdots + R_N \times W_N$$

FIG. 5

```
providing, by a light source, light to
illuminate a skin region                    — S61 detecting, by an optical sensing unit,
emergent light from the skin region and     — S62
outputting an intensity variation signal converting the intensity variation
signal to frequency domain data             — S63 calculating an SNR of the
frequency domain data                       — S64 determining a set of weightings and respiration
rate calculation algorithms according to the SNR  — S65 calculating a respiration rate according to the set of
weightings and respiration rate calculation algorithms  — S66
```

OPTICAL RESPIRATION RATE DETECTION DEVICE CAPABLE OF DETERMINING DENOISING RANGE

CROSS REFERENCE TO RELATED APPLICATION

This application is a divisional application of U.S. patent application Ser. No. 16/412,500 filed on, May 15, 2019, which is a continuation-in-part application of U.S. patent application Ser. No. 15/132,389 filed on, Apr. 19, 2016, which claims the priority benefit of Taiwan Patent Application Serial Number 104117736, filed on Jun. 1, 2015, the full disclosure of which is incorporated herein by reference.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

BACKGROUND

1. Field of the Disclosure

This disclosure generally relates to an optical physiological detection device and a detection method thereof, more particularly, to an optical respiration rate detection device using photoplethysmography signals and a detection method thereof.

2. Description of the Related Art

Conventional pulse oximeters utilize a non-invasive method to monitor the blood oxygenation and the heart rate of a user. A conventional pulse oximeter generally emits a red light beam (wavelength of about 660 nm) and an infrared light beam (wavelength of about 910 nm) to penetrate a part of the human body and detects an intensity variation of the penetrating light based on the feature that the oxyhemoglobin and the deoxyhemoglobin have different absorptivities in particular spectrum, e.g. referring to U.S. Pat. No. 7,072,701 and entitled "Method for spectrophotometric blood oxygenation monitoring". After the intensity variation of the penetrating light, e.g., photoplethysmography signals or PPG signals, of the two wavelengths is detected, the blood oxygenation can be calculated according to an equation Oxygen Saturation=$100\% \times [HbO_2]/([HbO_2]+[Hb])$, wherein $[HbO_2]$ is an oxyhemoglobin concentration and $[Hb]$ is a deoxy-hemoglobin concentration.

Generally, the intensity variation of the penetrating light of the two wavelengths detected by a pulse oximeter will increase and decrease with heartbeats. This is because blood vessels will expand and contract with heartbeats such that the blood volume through which the light beams pass will change to accordingly change the ratio of light energy being absorbed. Therefore, the heart rate of a user can be calculated according to the PPG signal.

In addition to the above oxygen saturation and the heart rate, the PPG signal can also be used to measure a respiration rate. However, the PPG signal generally has ultra low frequency noises which can degrade the accuracy of the respiration rate measurement.

SUMMARY

Accordingly, the present disclosure provides an optical respiration rate detection device with high detection accuracy and a detection method thereof.

The present disclosure provides an optical respiration rate detection device and a detection method thereof that previously categorize a respiration rate range of a current user to remove the noise interference thereby improving the detection accuracy.

The present disclosure further provides an optical respiration rate detection device and a detection method thereof that combine calculation results of different respiration rate algorithms using different weightings to improve the detection accuracy.

The present disclosure provides a respiration rate detection device including an optical sensing unit, an acceleration sensing unit and a processing unit. The optical sensing unit is configured to output an intensity variation signal. The acceleration sensing unit is configured to output an acceleration signal. The processing unit is configured to convert the intensity variation signal to a first frequency domain data and convert the acceleration signal to a second frequency domain data, determine a denoising range according to a second peak frequency in the second frequency domain data, remove the first frequency domain data within the denoising range of the first frequency domain data, and take a first peak frequency in the remained first frequency domain data as a respiration rate.

The optical respiration rate detection device of the present disclosure is a transmissive detection device or a reflective detection device.

BRIEF DESCRIPTION OF THE DRAWINGS

Other objects, advantages, and novel features of the present disclosure will become more apparent from the following detailed description when taken in conjunction with the accompanying drawings.

DETAILED DESCRIPTION OF THE EMBODIMENT

The illustration below includes embodiments of the present disclosure to clarify how the present disclosure is applied to actual conditions. It should be mentioned that elements not directly related to the present disclosure are omitted in the drawings. Meanwhile, to clarify the relationship between elements, scales of the element in the drawings may not be identical to actual scales.

Figure 1:
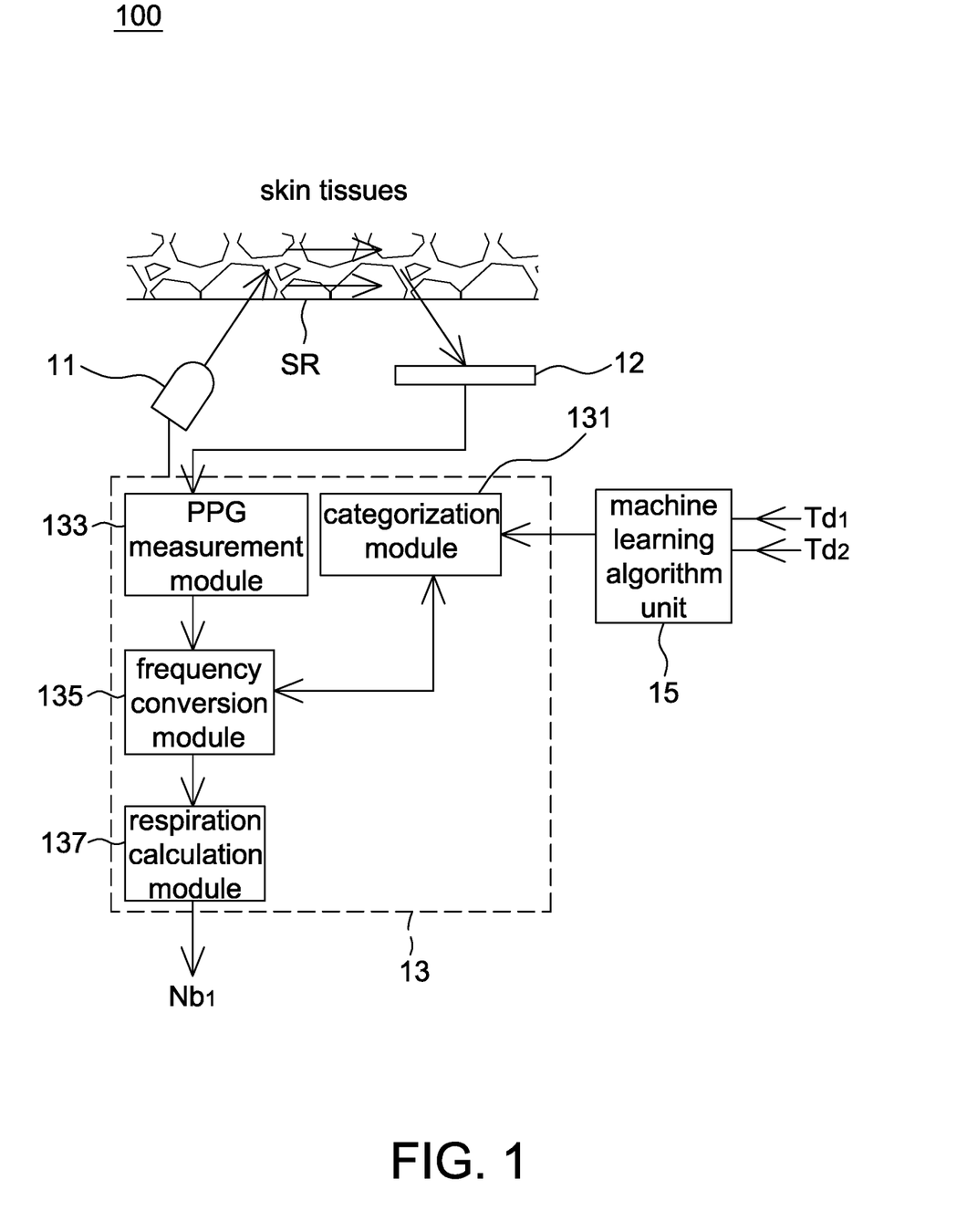
FIG. 1 is a schematic block diagram of a respiration rate detection device according to a first embodiment of the present disclosure.

Referring to FIG. 1, it is a schematic block diagram of a respiration rate detection device 100 according to a first embodiment of the present disclosure. The respiration rate detection device 100 categorizes currently detected photoplethysmography signals (or PPG signals) according to predetermined categorization data so as to remove the noise interference in a part of frequency zones thereby increasing the detection accuracy. The respiration rate detection device 100 includes a light source 11, an optical sensing unit 12 and a processing unit 13.

The light source 11 is selected from a coherent light source, a partially coherent light source or a non-coherent light source without particular limitations, e.g., a light emitting diode or a laser diode. The light source 11 provides light to illuminate a skin region SR. The light enters skin tissues under the skin region SR and then emerges from the skin region SR after propagating inside the skin tissues for a distance. In some embodiments, an illumination wavelength of the light source 11 is selected from those used in conventional pulse oximeters. In other embodiments, an illumination wavelength of the light source 11 is selected from 300 nm to 940 nm. It should be mentioned that, although FIG. 1 shows only one light source 11, it is only intended to illustrate but not to limit the present disclosure. In some embodiments, if the respiration rate detection device 100 is also used for detecting an oxygen saturation, two light sources respectively illuminating red light and infrared light are used. In other embodiments, if the respiration rate detection device 100 also has a calibration function, three light sources respectively illuminating green light, red light and infrared light are used, wherein the green light PPG signal is used to determine a filter parameter for filtering the red light PPG signal and the infrared light PPG signal.

The optical sensing unit 12 detects light emergent from the skin region SR and outputs an intensity variation signal. In some embodiments, the optical sensing unit 12 is a photodiode and the intensity variation signal outputted from the photodiode is used as the PPG signal. In some embodiments, the optical sensing unit 12 is an image sensor which has a pixel array including a plurality of pixels. Each pixel of the pixel array respectively outputs an intensity signal within a frame and the processing unit 13 further calculates a sum of the intensity signals outputted from a plurality of pixels within the frame, wherein a variation of the sum of the intensity signals with time is used as the PPG signal. In some embodiments, an intensity variation signal outputted by each pixel of the pixel array is used as the PPG signal, i.e. the pixel array outputting a plurality of intensity variation signals. In addition, in some embodiments when the optical sensing unit 12 is an image sensor, it is preferably an active image sensor, e.g., a CMOS image sensor. In the active image sensor, a window of interest is determined according to an actual intensity distribution detected by the pixel array thereof, wherein the processing unit 13 processes pixel data only within the window of interest but ignores pixel data outside the window of interest so as to improve the practicability thereof.

The processing unit 13 is, for example, an application specific integrated circuit (ASIC), a digital signal processor (DSP), a microcontroller (MCU) or a central processing unit (CPU) for receiving and post-processing the intensity variation signal outputted from the optical sensing unit 12. In this embodiment, the processing unit 13 converts the intensity variation signal to frequency domain data, categorizes the frequency domain data into one of a plurality of frequency zones according to predetermined categorization data, and calculates a respiration rate according to the frequency domain data of the categorized frequency zone.

The processing unit 13 includes, for example, a categorization module 131, a PPG measurement module 133, a frequency conversion module 135 and a respiration calculation module 137. It should be mentioned that although FIG. 1 shows functions performed by the processing unit 13 as different functional blocks, it is only intended to illustrate but not to limit the present disclosure. The functions performed by the categorization module 131, the PPG measurement module 133, the frequency conversion module 135 and the respiration calculation module 137 are all considered to be performed by the processing unit 13 and implemented by software, hardware or a combination thereof without particular limitations.

Figure 2A:
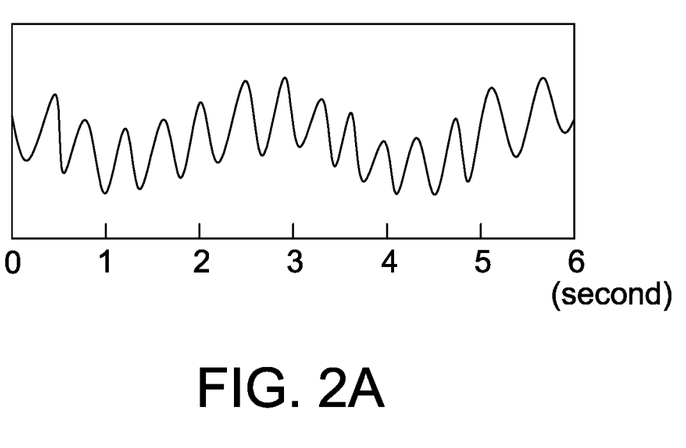
FIG. 2A is a schematic diagram of an intensity variation signal generated by a respiration rate detection device according to an embodiment of the present disclosure.
Figure 2B:
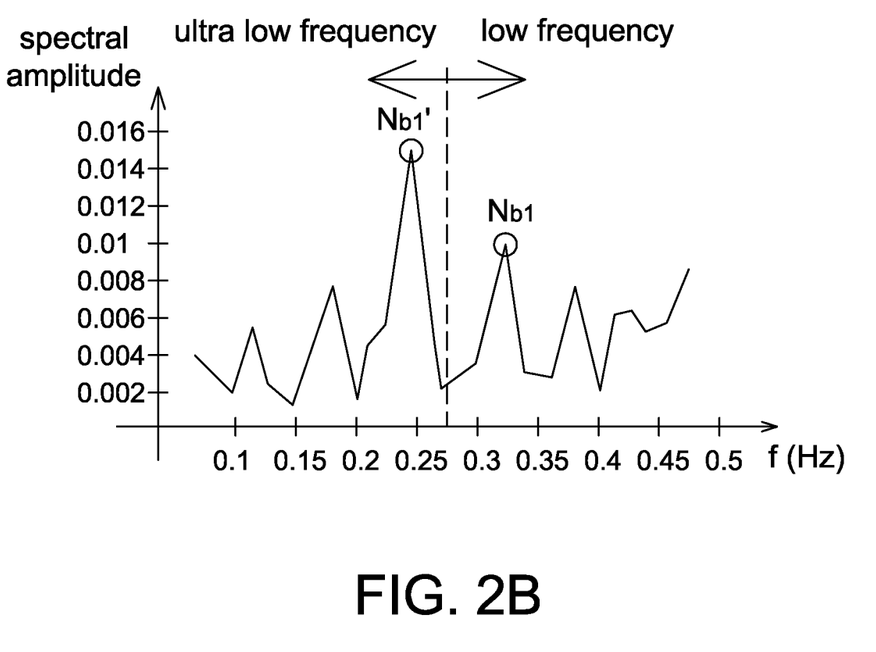
FIG. 2B is a schematic diagram of frequency domain data generated by a respiration rate detection device according to an embodiment of the present disclosure.

Referring to FIGS. 1 and 2A-2B, FIG. 2A is a schematic diagram of an intensity variation signal (or PPG signal) generated by a respiration rate detection device according to an embodiment of the present disclosure, and FIG. 2B is a schematic diagram of frequency domain data generated by a respiration rate detection device according to an embodiment of the present disclosure.

The PPG measurement module 133 receives the intensity variation signal from the optical sensing unit 12 and continuously acquires intensity signals within a time interval, e.g., 5 to 10 seconds, to be used as the PPG signal. For example, FIG. 2A shows the intensity variation signal within a time interval of 6 seconds to be used as the PPG signal. As the optical sensing unit 12 sequentially outputs intensity signals at a sample rate (or frame rate), the time intervals may or may not be overlapped with one another in time. For example, the PPG measurement module 133 takes the intensity variation signal between 1 to 7 seconds as a next PPG signal or takes the intensity variation signal between 7 to 13 seconds as a next PPG signal, and so on.

When the optical sensing unit 12 is a photodiode, the PPG measurement module 133 directly retrieves the intensity variation signal being outputted within a time interval as the PPG signal, wherein the PPG measurement module 133 does not perform any processing on the intensity variation signal or performs the pre-processing such as filtering or amplifying on the intensity variation signal. When the optical sensing unit 12 is an image sensor, the PPG measurement module 133 calculates a sum of intensity signals of at least a part of pixel data (e.g. pixel data within a window of interest) of every frame outputted by the pixel array, and continuously retrieves the sum of intensity signals within a time interval, e.g., 5 to 10 seconds, as the PPG signal as shown in FIG. 2A. In other embodiments, when the optical sensing unit 12 is an image sensor, the image sensor itself has the function of calculating the sum of intensity signals (e.g., implemented by circuit). In this case, the PPG measurement module 133 retrieves the sum of intensity signals within a time interval, e.g., 5 to 10 seconds, as the PPG signal. In this case, the PPG measurement module 133 does not perform any processing on the sum of intensity signals or performs the pre-processing such as filtering or amplifying on the sum of intensity signals. It should be mentioned that although FIG. 2A shows the intensity variation signal within 6 seconds being used as the PPG signal, it is only intended to illustrate but not to limit the present disclosure.

The frequency conversion module 135 converts the intensity variation signal (or PPG signal) into frequency domain data as shown in FIG. 2B, wherein the frequency conversion is selected from, for example, the fast Fourier transform (FFT) or discrete Fourier transform (DFT) without particular limitations.

As shown in FIG. 2B, if there is no ultra low frequency noise, the maximum spectral amplitude should appear at a position Nb1 in the frequency domain data. However, when ultra low frequency noises exist, another maximum spectral amplitude at a position Nb1' could exist in the frequency domain data to lead to a misidentification. Accordingly, the frequency conversion module 135 further sends the frequency domain data to the categorization module 131 to be compared with predetermined categorization data therein. The categorization module 131 categorizes the frequency domain data as one of a plurality of frequency zones, e.g., an ultra low frequency zone or a low frequency zone shown in FIG. 2B. In some embodiments, the categorization module 131 separates two frequency zones by an isolation frequency, wherein the isolation frequency is selected from a frequency range between 0.15 Hz and 0.25 Hz, but not limited thereto. It is appreciated that when the processing unit 13 separates more than two frequency zones, the isolation frequencies are selected from more than two frequency ranges.

In the present disclosure, the predetermined categorization data is previously built up by a machine learning algorithm, wherein the machine learning algorithm is implemented by, e.g., the neural network, support vector machine, random forest and so on without particular limitations. As shown in FIG. 1, a machine learning algorithm unit 15 previously receives a plurality of ultra low frequency learning data Td1 and low frequency learning data Td2 for learning so as to recognize data characteristics of different frequency zones, wherein the ultra low frequency learning data Td1 and the low frequency learning data Td2 are the frequency domain data obtained from the categorized (e.g., categorized ultra low frequency data or categorized low frequency data) PPG signal previously converted by the frequency conversion module 135. It is appreciated that when there are more frequency zones to be categorized (i.e. not limited to the ultra low frequency zone or low frequency zone), more types of the learning data (i.e. frequency domain data) are required. It should be mentioned that although FIG. 1 shows that the machine learning algorithm unit 15 is outside of the processing unit 13, e.g., in an external host or an external computer system, the present disclosure is not limited thereto. In other embodiments, the machine learning algorithm unit 15 is included inside the processing unit 13.

Finally, the respiration calculation module 137 calculates a respiration rate Nb1 according to the frequency domain data of the categorized frequency zone. For example, the respiration calculation module 137 takes a frequency corresponding to a maximum spectral amplitude in the categorized frequency zone as a respiration frequency (respiration rate). Referring to FIG. 2B, when the categorization module 131 categorizes current frequency domain data into the low frequency zone, the respiration calculation module 137 takes a frequency corresponding to the maximum spectral amplitude Nb1 therein as a current respiration rate, which is then outputted; when the categorization module 131 categorizes current frequency data as the ultra low frequency zone, the respiration calculation module 137 takes a frequency corresponding to the maximum spectral amplitude Nb1' therein as a current respiration rate, which is then outputted.

In this embodiment, the processing unit 13 ignores the frequency domain data outside the categorized frequency zone. For example, when the frequency domain data is categorized as the low frequency zone, the frequency domain data in the ultra low frequency zone is ignored; whereas, when the frequency domain data is categorized as the ultra low frequency zone, the frequency domain data in the low frequency zone is ignored. In addition, the operation of embodiments having more frequency zones is similar. It is possible to implement the ignoring as below.

In one embodiment, the frequency conversion module 135 provides current frequency domain data to the categorization module 131 to be compared with predetermined categorization data therein and categorized. The categorization module 131 informs the frequency conversion module 135 of the categorized result to allow the frequency conversion module 135 to provide the frequency domain data only in the categorized frequency zone to the respiration calculation module 137. Accordingly, the respiration calculation module 137 will not process the frequency domain data outside the categorized frequency zone.

In another embodiment, the frequency conversion module 135 provides all current frequency domain data to the respiration calculation module 137, and the categorization module 131 provides categorization information to the respiration calculation module 137. Accordingly, when a current respiration rate obtained by the respiration calculation module 137 is within a categorized frequency zone, the current respiration rate is outputted; whereas, when the current respiration rate obtained by the respiration calculation module 137 is not within the categorized frequency zone, a frequency corresponding to a next maximum spectral amplitude is calculated and confirmed with the categorized frequency zone till a current respiration rate within the categorized frequency zone is obtained and the current respiration rate within the categorized frequency zone is then outputted. Or the respiration calculation module 137 calculates the current respiration rate according to the frequency domain data only within a categorized frequency zone but ignores the frequency domain data outside the categorized frequency zone.

Figure 3:
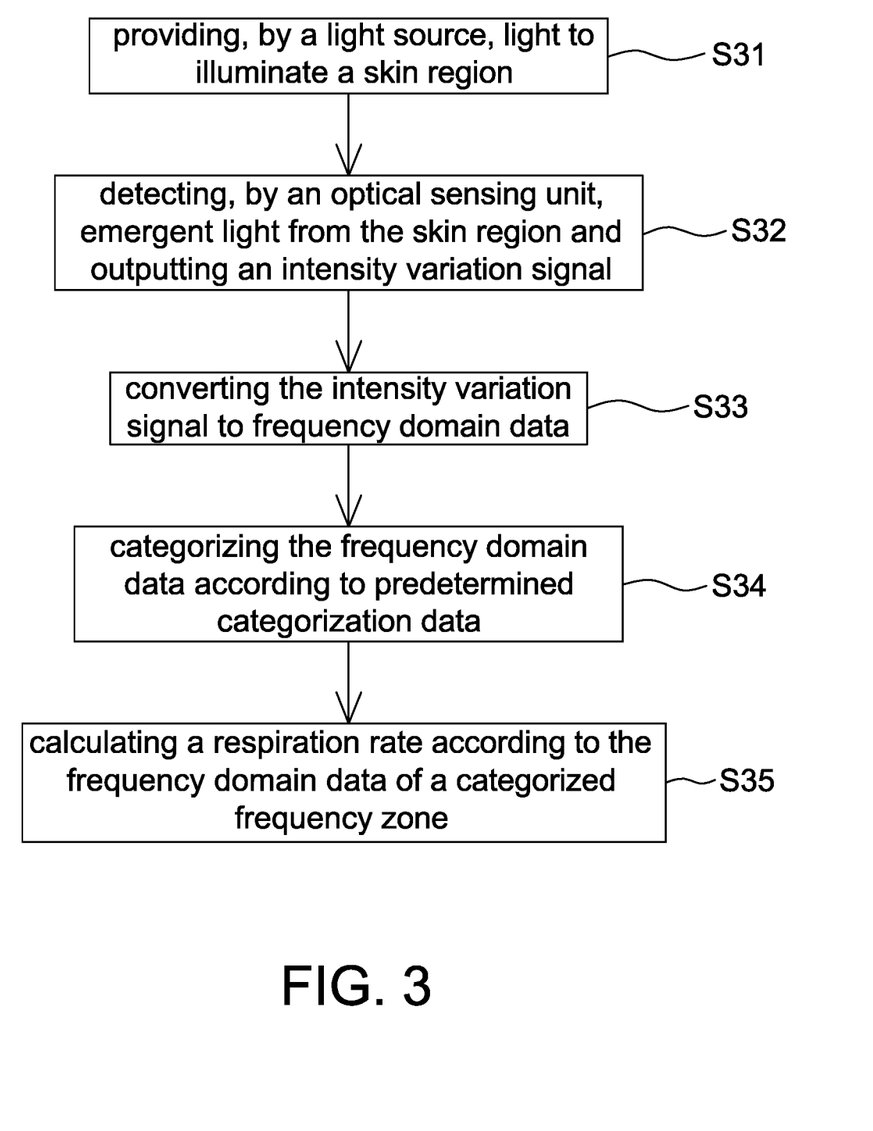
FIG. 3 is a flow chart of a respiration rate detection method according to a first embodiment of the present disclosure.

Referring to FIG. 3, it is a flow chart of a respiration rate detection method according to a first embodiment of the present disclosure including the steps of: providing, by a light source, light to illuminate a skin region (Step S31); detecting, by an optical sensing unit, emergent light from the skin region and outputting an intensity variation signal (Step S32); converting the intensity variation signal to frequency domain data (Step S33); categorizing the frequency domain data according to predetermined categorization data (Step S34); and calculating a respiration rate according to the frequency domain data of a categorized frequency zone (Step S35). The respiration rate detection method of this embodiment is applicable, for example, to the respiration rate detection device 100 of FIG. 1, and since details of implementation have been illustrated above, details thereof are not repeated herein.

By using the respiration rate detection device and the respiration rate detection method of the first embodiment of the present disclosure, the interference from noises outside the categorized frequency zone is removed thereby improving the detection accuracy.

Figure 4:
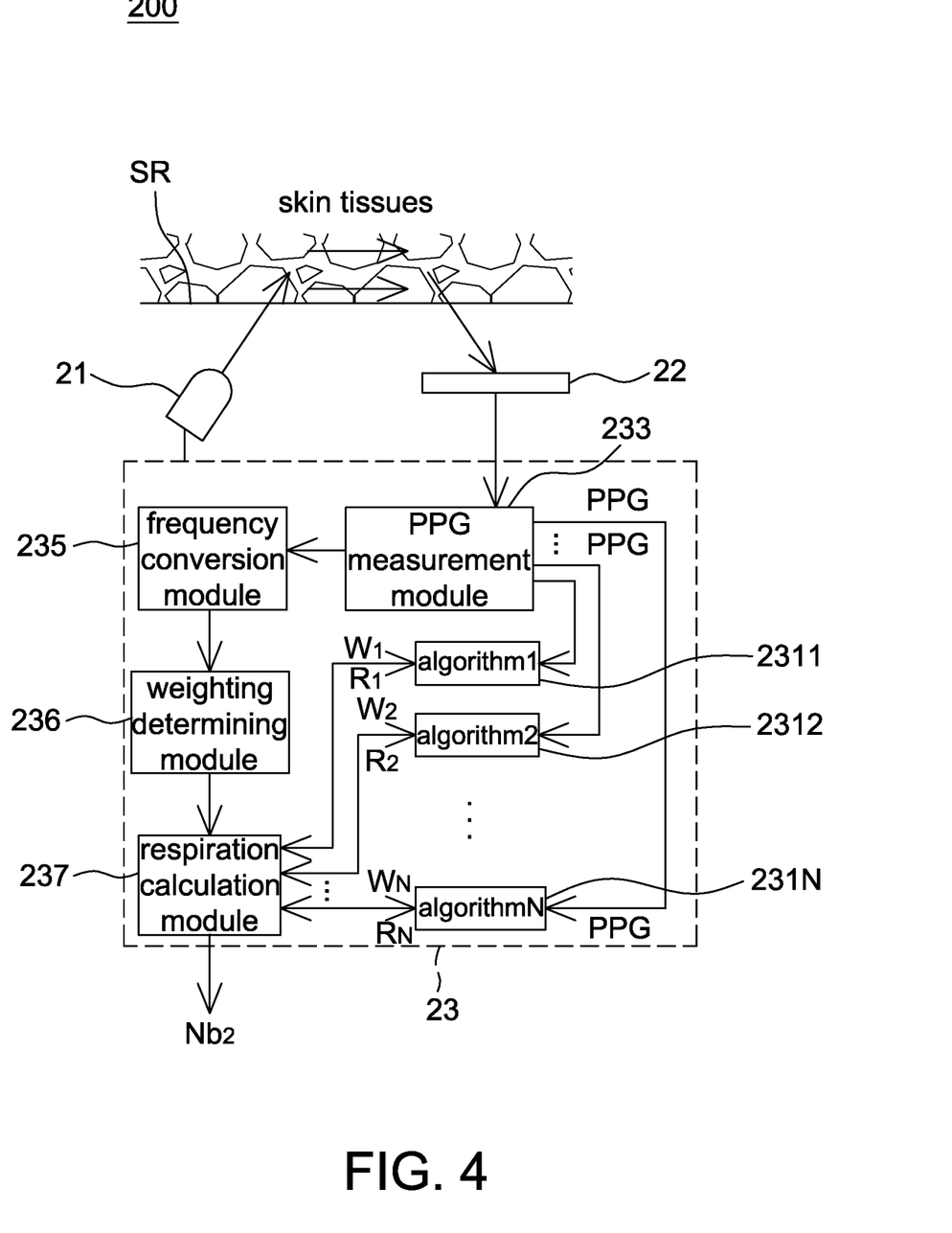
FIG. 4 is a schematic block diagram of a respiration rate detection device according to a second embodiment of the present disclosure.

Referring to FIG. 4, it is a schematic block diagram of a respiration rate detection device 200 according to a second embodiment of the present disclosure. The respiration rate detection device 200 determines a set of weightings and a set of respiration rate calculation algorithms according to a main frequency amplitude of a current PPG signal, takes respiration rates obtained by different respiration rate calculation algorithms as respiration rate components, and combines the respiration rate components according to the set of weightings to form an output respiration rate thereby improving the detection accuracy. The respiration rate detection device 200 includes a light source 21, an optical sensing unit 22 and a processing unit 23, wherein the light source 21 and the optical sensing unit 22 are similar to those of the first embodiment and thus details thereof are not repeated herein.

In this embodiment, the processing unit 23 is also selected from a digital signal processor (DSP), a microcontroller (MCU) or a central processing unit (CPU), and used to receive an intensity variation signal outputted from the optical sensing unit 12 and perform the post-processing. The processing unit 23 converts the intensity variation signal into frequency domain data, determines a set of weightings and a set of respiration rate calculation algorithms according to a signal to noise ratio (SNR) of the frequency domain data, and calculates a respiration rate according to the set of weightings and the set of respiration rate calculation algorithms.

The processing unit 23 includes a PPG measurement module 233, a frequency conversion module 235, a weighting determining module 236, a respiration calculation module 237 and a plurality of respiration rate calculation units 2311 to 231N, wherein the function of the PPG measurement module 233 is similar to the PPG measurement module 133 of the first embodiment and thus details thereof are not repeated herein. The frequency conversion module 235 converts the PPG signal (e.g., shown in FIG. 2A) outputted by the PPG measurement module 233 into frequency domain data (e.g., shown in FIG. 2B). It should be mentioned that although FIG. 4 shows functions performed by the processing unit 23 as different functional blocks, it is only intended to illustrate but not to limit the present disclosure. The functions performed by the PPG measurement module 233, the frequency conversion module 235, the weighting determining module 236, the respiration calculation module 237 and the plurality of respiration rate calculation units 2311 to 231N are all considered to be executed by the processing unit 23 and implemented by software, hardware or a combination thereof without particular limitations.

In the present disclosure, respiration rate calculation algorithms include, for example, directly performing the Fourier spectrum analysis on the PPG signal, acquiring respiration characteristics in the PPG signal (e.g. characteristics of amplitude variation or frequency variation) and then performing the Fourier spectrum analysis on the respiration characteristics, the independent component analysis and the adaptive noise filtering, without particular limitations. The respiration rate calculation algorithms also include the self-designed respiration rate calculation algorithm which calculates a current respiration rate in time domain or frequency domain. Any respiration rate calculation algorithms are applicable to the respiration rate detection device 200 as long as different respiration rate calculation algorithms correspond to different signal features, e.g., the signal to noise ratio or energy distribution, wherein said different signal features are used to determine the weighting corresponding to the associated respiration rate calculation algorithm. For example, although a distortion is not obvious by directly performing the Fourier spectrum analysis on the PPG signal, the result is easily influenced by ultra low frequency noises. Accordingly, when the respiration rate component obtained by the Fourier spectrum analysis is within an ultra low frequency zone, the weighting corresponding to the Fourier spectrum analysis is reduced so as to reduce the interference from noises within the ultra low frequency zone.

In one embodiment, it is assumed that the above four respiration rate calculation algorithms are used, and the weighting corresponding to each respiration rate calculation algorithm is assumed to be 1 at first. If a signal to noise ratio of the obtained frequency domain data is lower than a first threshold (e.g., threshold1), it means that the noise is obvious such that the weighting corresponding to the adaptive noise filtering is increased (e.g., increasing the weighting by 1). If the signal to noise ratio of the obtained frequency domain data is higher than a second threshold (e.g., threshold2), it means that the noise is not obvious such that the weighting corresponding to directly performing the Fourier spectrum analysis on the PPG signal is increased (e.g., increasing the weighting by 1). If a sum of spectral amplitudes of ultra low frequency signals (or a ratio of the sum of spectral amplitudes of ultra low frequency signals with respect to a sum of spectral amplitudes of low frequency signals) is higher than a third threshold (e.g., threshold3), it means that the respiration characteristics in the PPG signal are easily interfered by ultra low frequency noises such that the weighting corresponding to acquiring respiration characteristics in the PPG signal and then performing the Fourier spectrum analysis on the respiration characteristics is decreased (e.g., decreasing the weighting by 1) and/or the weighting corresponding to the independent component analysis is increased (e.g., increasing the weighting by 1). If a sum of spectral amplitudes of ultra low frequency signals (or a ratio of the sum of spectral amplitudes of ultra low frequency signals with respect to a sum of spectral amplitudes of low frequency signals) is lower than a fourth threshold (e.g., threshold4), the weighting corresponding to acquiring respiration characteristics in the PPG signal and then performing the Fourier spectrum analysis on the respiration characteristics is increased (e.g., increasing the weighting by 1).

Figure 5:
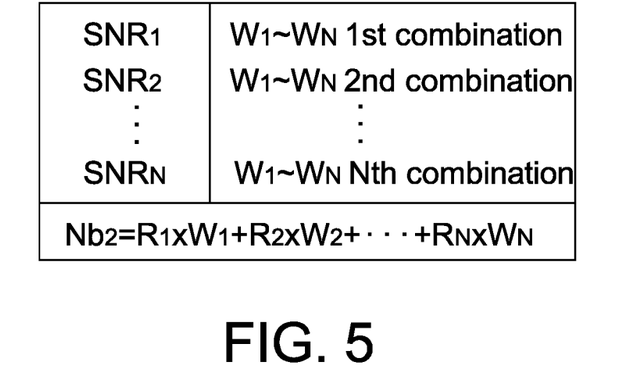
FIG. 5 is a schematic diagram of a look-up table of a respiration rate detection device according a second embodiment of the present disclosure.

Next, referring to FIGS. 2B, 4-5, FIG. 5 is a schematic diagram of a look-up table of a respiration rate detection device according a second embodiment of the present disclosure.

The weighting determining module 236 determines a set of weightings and a set of respiration rate calculation algorithms according to a signal to noise ratio (SNR) of the frequency domain data. In some embodiments, the signal to noise ratio is a ratio of a maximum spectral amplitude with respect to a sum of other spectral amplitudes in the frequency domain data. For example in FIG. 2B, the signal to noise ratio is a ratio of a spectral amplitude at Nb1' with respect to a sum of other spectral amplitudes. Accordingly, after the weighting determining module 236 obtains a signal to noise ratio, the signal to noise ratio is compared with a look-up table as shown in FIG. 5, wherein the relationship of a plurality of signal to noise ratios with respect to a plurality of weightings is previously built up to form the look-up table. In other words, the processing unit 23 is built in a plurality of respiration rate calculation algorithms (e.g., 2311 to 231N), and the selected set of respiration rate calculation algorithms includes at least one of the stored respiration rate calculation algorithms, and each signal to noise ratio (e.g., $SNR_1$ to $SNR_N$) corresponds to a set of weightings and an associated set of respiration rate calculation algorithms. It should be mentioned that although FIG. 5 shows the relationship of a plurality of signal to noise ratios with respect to a plurality of weightings, it is only intended to illustrate but not to limit the present disclosure. In some embodiments, the look-up table stores the relationship of a plurality of signal to noise ratio ranges with respect to a plurality of weightings. In other embodiments, the look-up table stores the relationship of a plurality of signal to noise ratios (or signal to noise ratio ranges) and frequency zones with respect to a plurality of weightings. In the present disclosure, the weighting may be between 0 and 1. In other words, when the weighting corresponding to one respiration rate calculation algorithm is 0, it means that the respiration rate calculation algorithm is not used. In other embodiments, the look-up table stores the relationship of a plurality of energy distributions (e.g., a sum of spectral amplitudes of ultra low frequency signals, a ratio of a sum of spectral amplitudes of ultra low frequency signals with respect to a sum of spectral amplitudes of low frequency signals) with respect to a plurality of weightings.

Finally, the respiration calculation module 237 calculates a respiration rate Nb2 according to the selected set of weightings and the selected set of respiration rate calculation algorithms. In one embodiment, each algorithm of the selected set of respiration rate calculation algorithms respectively calculates a respiration rate component $R_1, R_2 \ldots R_N$ according to the intensity variation signal. For example, the respiration rate Nb2 is a sum of products of each of the selected set of weightings $W_1, W_2 \ldots W_N$ and each of the respiration rate component $R_1, R_2 \ldots R_N$ obtained by the associated respiration rate calculation algorithm, i.e. $Nb2=R_1 \times W_1 + R_2 \times W_2 + \ldots + R_N \times W_N$, wherein at least one of $R_1, R_2 \ldots R_N$ is not zero. In other words, according to actually acquired frequency domain data, it is possible that the respiration calculation module 237 calculates a current respiration rate according to one respiration rate calculation algorithm, and in this case the weighting corresponding to the one respiration rate calculation algorithm is set to 1 and the weightings corresponding to other respiration rate calculation algorithms are set to zero. That is, the above respiration rate components are the respiration rates obtained by every respiration rate calculation algorithm, and when a set of respiration rate calculation algorithms includes more than one respiration rate calculation algorithms, the respiration rate obtained by each of the more than one respiration rate calculation algorithms is not directly used as an output respiration rate and referred as a respiration rate component herein. When a set of respiration rate calculation algorithms includes one respiration rate calculation algorithm, the respiration rate component obtained by the one respiration rate calculation algorithm is used as an output respiration rate.

Figure 6:
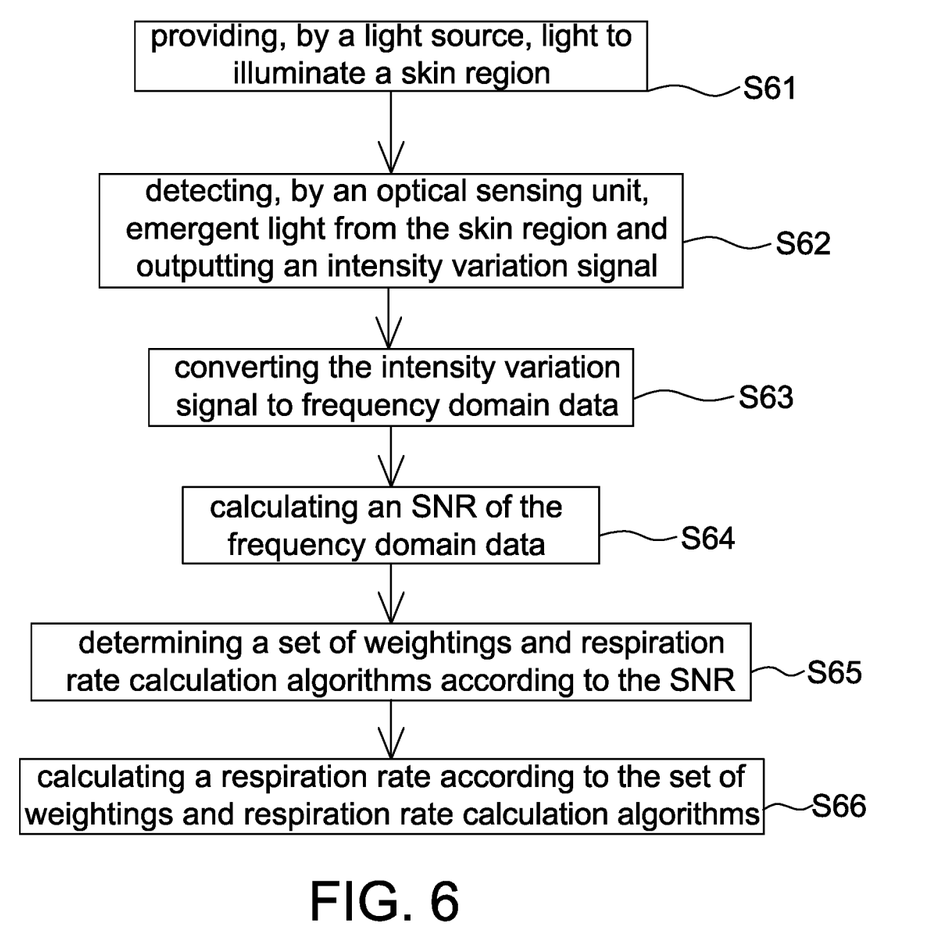
FIG. 6 is a flow chart of a respiration rate detection method according to a second embodiment of the present disclosure.

Referring to FIG. 6, it is a flow chart of a respiration rate detection method according to a second embodiment of the present disclosure including the steps of: providing, by a light source, light to illuminate a skin region (Step S61); detecting, by an optical sensing unit, emergent light from the skin region and outputting an intensity variation signal (Step S62); converting the intensity variation signal to frequency domain data (Step S63); calculating a signal to noise ratio of the frequency domain data (Step S64); determining a set of weightings and a set of respiration rate calculation algorithms according to the signal to noise ratio (Step S65); and calculating a respiration rate according to the set of weightings and the set of respiration rate calculation algorithms (Step S66). The respiration rate detection method of this embodiment is applicable to the respiration rate detection device 200 of FIG. 4.

Referring to FIGS. 2A-2B and 4-6, details of this embodiment are illustrated hereinafter.

Step S61: The light source 21 emits light of a predetermined optical spectrum to illuminate a skin region SR. As described in the first embodiment, corresponding to different applications, it is possible that the respiration rate detection device 200 includes more than one light source.

Step S62: The optical sensing unit 22 detects emergent light from the skin region SR and outputs an intensity variation signal. As described in the first embodiment, the optical sensing unit 22 is a light emitting diode or an image sensor having a pixel array.

Step S63: As described in the first embodiment, the PPG measurement module 233 continuously acquires the intensity variation signal within a time interval (e.g., 5 to 10 seconds) to be used as the PPG signal, wherein according to different embodiments of the optical sensing unit 22, the intensity variation signal is the intensity signals or a sum of intensity signals within a time interval. The frequency conversion module 235 converts the intensity variation signal (or the PPG signal) into frequency domain data.

Step S64: The weighting determining unit 236 calculates a signal to noise ratio of the frequency domain data at first. For example, the weighting determining unit 236 determines a main frequency, e.g., Nb1' shown in FIG. 2B having a maximum spectral amplitude and taken as the main frequency, in the frequency domain data at first. Then, the weighting determining unit 236 calculates a ratio of a spectral amplitude of the main frequency with respect to a sum of other spectral amplitudes in the frequency domain data to be used as the signal to noise ratio herein.

Step S65: Then, the weighting determining unit 236 compares the signal to noise ratio with a look-up table (as shown in FIG. 5) to determine a set of weightings and a set of respiration rate calculation algorithms. As mentioned above, the look-up table previously stores the relationship of a plurality of signal to noise ratios (or a plurality of signal to noise ranges) with respect to a plurality of weightings, e.g., storing in a memory of the processing unit 23. Accordingly, when the weighting determining unit 236 obtains a signal to noise ratio, a set of weightings and a set of respiration rate calculation algorithms are determined correspondingly.

After the set of respiration rate calculation algorithms is determined, each algorithm of the determined set of respiration rate calculation algorithms respectively calculates a respiration rate component $R_1, R_2 \ldots R_N$ according to the intensity variation signal (or the PPG signal). It is appreciated that the respiration rate calculation algorithm not included in the selected set of respiration rate calculation algorithms does not operate so as to reduce the system resources.

Step S66: Finally, the respiration calculation module 237 calculates a sum of products of each of the set of weightings $W_1, W_2 \ldots W_N$ and each of the respiration rate components $R_1, R_2 \ldots R_N$ obtained by the set of respiration rate calculation algorithms corresponding to the set of weightings, e.g., $Nb2=R_1 \times W_1 + R_2 \times W_2 + \ldots + R_N \times W_N$, and the sum of products Nb2 is then outputted.

In the present disclosure, the respiration rate Nb1 or Nb2 outputted by the processing unit 13 or 23 is applicable to different applications, e.g., being displayed, being compared with at least one threshold, being recorded and so on without particular limitations.

In some embodiments, the respiration rate detection methods in the above first and second embodiments are combinable to further improve the detection accuracy. For example, the first embodiment is initially used to remove the frequency domain data in some frequency zones, and then the second embodiment is used to calculate the frequency domain data being left (e.g., the frequency domain data in the ultra low frequency zone or in the low frequency zone shown in FIG. 2B). Details of the two embodiments are illustrated above, and thus details thereof are not repeated herein.

It should be mentioned that although FIGS. 1 and 4 show that the light sources 11 and 21 and the optical sensing units 12 and 22 are located at a same side of a skin region SR to form a reflective detection device, it is only intended to illustrate but not to limit the present disclosure. In other embodiments, the light source and the optical sensing unit are located at opposite sides of the skin region to form a transmissive detection device.

As mentioned above, the PPG signal sometimes includes ultra low frequency noises to degrade the detection accuracy. Accordingly, the present disclosure further provides a respiration rate detection device that utilizes the detection result of an acceleration sensor to confirm a respiration rate.

Figure 7:
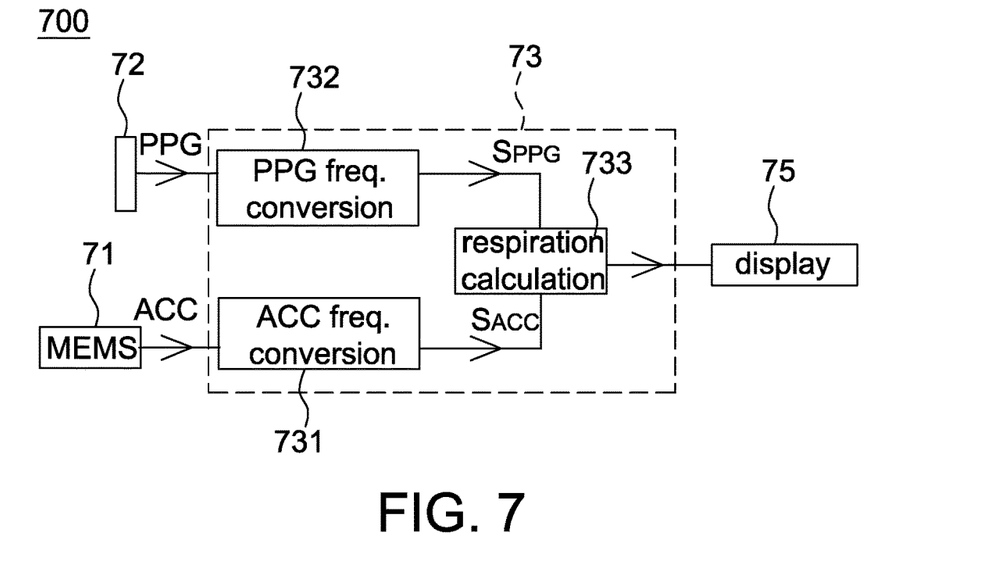
FIG. 7 is a schematic block diagram of a respiration rate detection device according to a third embodiment of the present disclosure.

Referring to FIG. 7, it a schematic block diagram of a respiration rate detection device 700 according to a third embodiment of the present disclosure including an acceleration sensing unit 71, an optical sensing unit 72 and a processing unit 73 electrically coupled to the two sensing units. The respiration rate detection device 700 further includes a light source as mentioned above, and thus details thereof are not repeated herein.

The respiration rate obtained by the respiration rate detection device 700 is transmitted to a display 75 via a wired or wireless communication interface (not shown in FIG. 7) to be shown thereon using numbers or graphs. The display 75 is included in or separated from the respiration rate detection device 700.

The optical sensing unit 72 of this embodiment is identical to the optical sensing unit 12 shown in FIG. 1 and also used to output an intensity variation signal (or referred to PPG signal). The optical sensing unit 72 is a photodiode or a CMOS image sensor as mentioned above, and thus details thereof are not repeated herein.

The acceleration sensing unit 71 is, for example, a MEMS acceleration sensor, a G-sensor or the like, and is used to output an acceleration signal ACC. The acceleration sensing unit 71 is preferably arranged close to or adjacent to the optical sensing unit 72 and operates simultaneously with the optical sensing unit 72. More specifically, within a detection time-interval, the optical sensing unit 72 outputs a time-varied intensity variation signal PPG and the acceleration sensing unit 71 outputs a time-varied acceleration signal ACC to the processing unit 73 for the post-processing, e.g., filtering, comparing and calculation.

Similar to the processing unit 13, the processing unit 73 is also an ASIC or a DSP that performs the calculation using a hardware and/or software. The processing unit 73 also includes a PPG frequency conversion module 732 (operating similar to 135) used to convert the intensity variation signal PPG to a first frequency domain data, e.g., the PPG spectrum $S_{PPG}$ shown in FIG. 8. The processing unit 73 further includes an acceleration (ACC) frequency conversion module 731 used to convert the acceleration signal ACC to a second frequency domain data, e.g., the ACC spectrum $S_{ACC}$ shown in FIG. 8.

Figure 8:
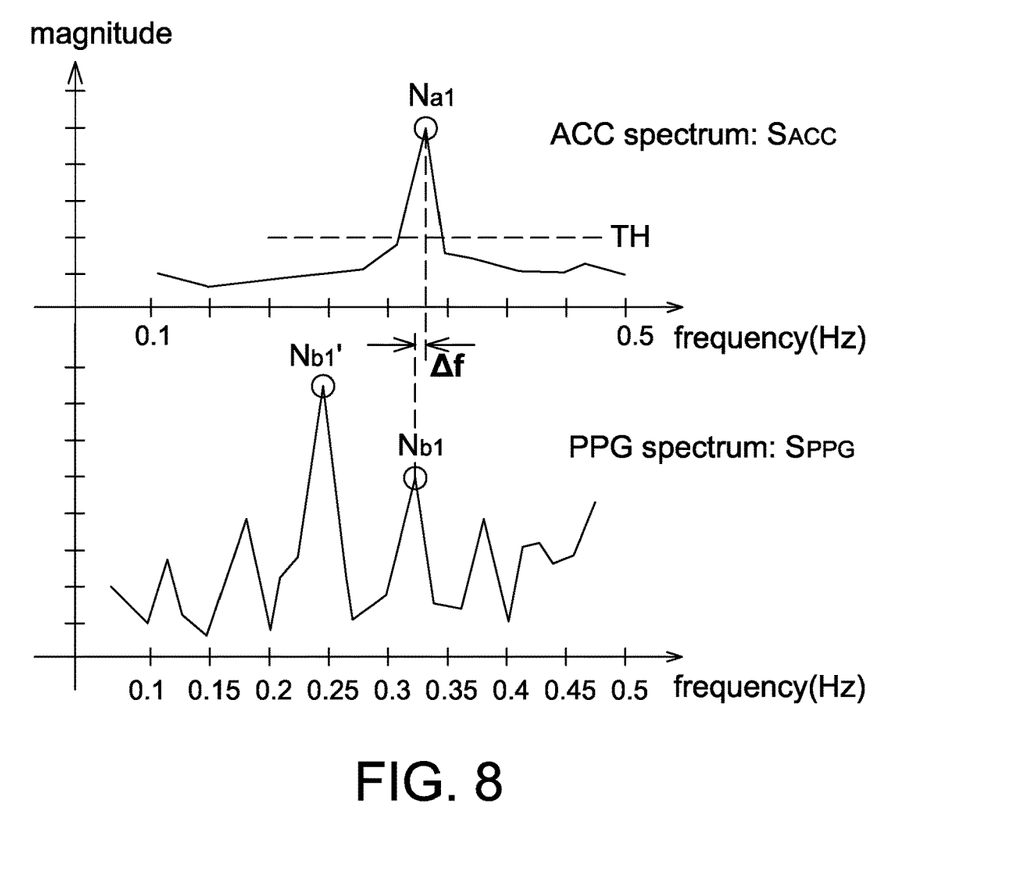
FIG. 8 is an operational schematic diagram of a respiration rate detection device according to a third embodiment of the present disclosure.

FIG. 8 is an operational schematic diagram of a respiration rate detection device 700 according to a third embodiment of the present disclosure. The processing unit 73 further includes a respiration calculation circuit 733 used to confirm a correct respiration rate and eliminate noises according to the first frequency domain data $S_{PPG}$ and the second frequency domain data $S_{ACC}$. It is appreciated that although FIG. 7 shows three separated blocks, operations of these three separated blocks are all considered executed by the processing unit 73.

In one aspect, the processing unit 73 is used to determine a frequency range according to a second peak frequency (e.g., a frequency corresponding to Na1 shown in FIG. 8) in the second frequency domain data $S_{ACC}$, and calculate a respiration rate according to a first peak frequency (e.g., a frequency corresponding to Nb1 shown in FIG. 8) within the determined frequency range of the first frequency domain data $S_{PPG}$. As noises in the PPG signal contain a double frequency and a half frequency of the respiration rate, the frequency range is preferably set as a range of 0.1 Hz taking the second peak frequency Na1 as a center thereof. If the respiration rate of a user changes, the second peak frequency and the corresponding frequency range are also changed.

In another aspect, the processing unit 73 is used to calculate a second peak value (e.g., Na1) within a predetermined frequency range of the second frequency domain data $S_{ACC}$, and determine a first peak frequency of a first peak value (e.g., Nb1) in the first frequency domain data $S_{PPG}$ corresponding to the second peak value Na1. Finally, the processing unit 73 calculates a respiration rate according to the first peak frequency.

As mentioned above, as the respiration rate is within a predetermined range, the predetermined frequency range is preferably set between 0.1 Hz and 0.5 Hz, or set adaptably corresponding to different users manually or automatically.

In this aspect, the first peak value Nb1 corresponding to the second peak value Na1 is, for example, referred to that (i) the two peaks Na1 and Nb1 have a frequency difference Δf smaller than 0.05 Hz, (ii) the overlapping of a full-width at half maximum (FWHM) of a spectrum shape of the second peak with that of the first peak is larger than a predetermined threshold or a predetermined ratio, or (iii) select one of multiple peak values in the first frequency domain data $S_{PPG}$ closest to the second peak value Na1, e.g., Nb1 instead of Nb'.

In another aspect, the processing unit 73 is used to determine a denoising range according to a second peak frequency (e.g., the frequency corresponding to Na1) in the second frequency domain data $S_{ACC}$, and remove the first frequency domain data of the first frequency domain data $S_{PPG}$ within the determined denoising range. Finally, the processing unit 73 takes a first peak frequency in the remained (i.e. out of the denoising range) first frequency domain data as a respiration rate.

As mentioned above, some noises in the first frequency domain data $S_{PPG}$ come from a double frequency and a half frequency of the respiration rate. Accordingly, the denoising range is preferably set as a frequency range outside 0.05 Hz from the second peak frequency, e.g., 0.1 Hz to (Na1−0.05 Hz) and (Na1+0.05 Hz) to 0.5 Hz. The second peak frequency Na1 is arranged as a center of the denoising range. For example, the processing unit 73 removes the first frequency domain data within the denoising range from a memory or a buffer. In the case that the remained first frequency domain data does not have a peak value, the processor 37 increases the denoising range (e.g., from 0.05 Hz to 0.1 Hz each side) in a next intensity variation signal PPG to keep more first frequency domain data.

To further reduce the memory space and increase the processing speed, within a predetermined time interval after the denoising ranged is determined, the processing unit 73 further performs a discrete Fourier transform (DFT) on the intensity variation signal PPG within a remained (out of the denoising range) frequency range without converting the data using the indices within the denoising range.

When using the respiration rate detection device 700 of the third embodiment to measure a respiration rate, the user is preferably in a steady status to obtain a clear second frequency domain data $S_{ACC}$. In addition, to eliminate the noises caused by slight motion (e.g. finger movement) of the user during measurement, the processing unit 73 is further used to ignore acceleration data in the acceleration signal ACC associated with an acceleration value or a slope of acceleration variation (in the time domain) larger than a predetermined threshold, the acceleration value is too high or the slope is too large. This is because that the acceleration, which is caused by the user's breathing, measured by the acceleration sensing unit 71 generally have smoothing acceleration values instead of abruptly changed values.

In the third embodiment, if the acceleration sensing unit 71 does not detect a clear acceleration peak, e.g., the second frequency domain data $S_{ACC}$ not containing any second peak value larger than an amplitude threshold TH, the second frequency domain data $S_{ACC}$ containing more than one peak larger than an amplitude threshold TH or the SNR thereof being too high, the processing unit 73 calculates the respiration rate according to the method in the first embodiment or the second embodiment. For example, the processing unit 73 categorizes the first frequency domain data $S_{PPG}$ as one of a plurality of frequency zones according to predetermined categorization data, and calculates a respiration rate using the first frequency domain data $S_{PPG}$ within the categorized frequency zone. Or, the processing unit 73 determines a set of weightings associated with a set of respiration rate calculation algorithms according to a sum of spectral amplitudes of the first frequency domain data $S_{PPG}$ lower than a predetermined frequency (e.g., 0.25 Hz, but not limited to), and calculates a respiration rate according to the set of weightings and the set of respiration rate calculation algorithms. Details thereof have been illustrated above, and thus are not repeated herein.

Furthermore, since the respiration rate generally does not exceed a rage between 0.1 Hz and 0.5 Hz, the processing unit 37 further firstly filters the first frequency domain data $S_{PPG}$ and the second frequency domain data $S_{ACC}$ using a digital filter having a pass band between 0.1 Hz and 0.5 Hz after obtaining the first frequency domain data $S_{PPG}$ and the second frequency domain data $S_{ACC}$, and then calculates the respiration rate using the above methods so as to improve the accuracy.

In the present disclosure, the peak value is referred to maximum spectral amplitude within the concerned frequency spectrum.

As mentioned above, the calculation of a respiration rate using PPG signals can be influenced by ultra low frequency noises to degrade the detection accuracy. Therefore, the present disclosure further provides a respiration rate detection device (FIGS. 1 and 4) and a respiration rate detection method (FIGS. 3 and 6) that improve the detection accuracy by the previous categorization or combining calculation results of different algorithms.

Although the disclosure has been explained in relation to its preferred embodiment, it is not used to limit the disclosure. It is to be understood that many other possible modifications and variations can be made by those skilled in the art without departing from the spirit and scope of the disclosure as hereinafter claimed.

What is claimed is:

1. A respiration rate detection device, comprising:
 an optical sensing unit configured to output an intensity variation signal;
 an acceleration sensing unit configured to output an acceleration signal; and
 a processing unit configured to
  convert the intensity variation signal to a first frequency domain data and convert the acceleration signal to a second frequency domain data,
  determine a denoising range according to a second peak frequency in the second frequency domain data,
  remove the first frequency domain data of the first frequency domain data within the denoising range, and
  take a first peak frequency in the remained first frequency domain data as a respiration rate when the peak value of the second peak frequency is larger than an amplitude threshold, and
  categorize the first frequency domain data as one of a plurality of frequency zones by comparing the first frequency domain data with predetermined categorization data of each of the plurality of frequency zones, and calculate the respiration rate using the first frequency domain data within a categorized frequency zone among the plurality of frequency zones when the second frequency domain data does not contain any second peak frequency with peak value larger than the amplitude threshold.

2. The respiration rate detection device as claimed in claim 1, wherein the denoising range is a frequency range outside 0.05 Hz from the second peak frequency, which is taken as a center of the denoising range.

3. The respiration rate detection device as claimed in claim 1, wherein the processing unit is further configured to ignore acceleration data in the acceleration signal associated with an acceleration value or a slope of acceleration variation larger than a predetermined threshold.

4. The respiration rate detection device as claimed in claim 1, wherein within a predetermined time interval after the denoising ranged is determined, the processing unit is further configured to perform a discrete Fourier transform on the acceleration signal within a remained frequency range.

5. The respiration rate detection device as claimed in claim 1, wherein the processing unit further configured to filter the first frequency domain data and the second frequency data with a filter having a pass band between 0.1 Hz and 0.5 Hz.

6. The respiration rate detection device as claimed in claim 1, wherein when the second frequency domain data does not contain any second peak frequency with peak value larger than the amplitude threshold, the processing unit is further configured to
 determine a set of weightings associated with a set of respiration rate calculation algorithms according to a sum of spectral amplitudes of the first frequency domain data lower than a predetermined frequency, and
 calculate the respiration rate according to the set of weightings and the set of respiration rate calculation algorithms.

7. The respiration rate detection device as claimed in claim 1, wherein the predetermined categorization data is previously built up by a machine learning algorithm based on learning data of each of the plurality of frequency zones.

* * * * *